(12) United States Patent
Arai

(10) Patent No.: US 6,306,608 B1
(45) Date of Patent: Oct. 23, 2001

(54) ANTI-HUMAN LECT2 ANTIBODY, CELLS PRODUCING THE SAME, AND METHOD AND KIT FOR ASSAYING THE SAME

(75) Inventor: Takao Arai, Noda (JP)

(73) Assignee: Medical & Biological Laboratories Co., Ltd., Nagoya (JP)

( * ) Notice: Subject to any disclaimer, the term of this patent is extended or adjusted under 35 U.S.C. 154(b) by 0 days.

(21) Appl. No.: 09/194,139

(22) PCT Filed: May 26, 1997

(86) PCT No.: PCT/JP97/01775

§ 371 Date: Nov. 25, 1998

§ 102(e) Date: Nov. 25, 1998

(87) PCT Pub. No.: WO97/45451

PCT Pub. Date: Dec. 4, 1997

(30) Foreign Application Priority Data

May 27, 1996 (JP) .................................................... 8-132160

(51) Int. Cl.[7] ............................ C12Q 1/00; G01N 33/53; G01N 33/537; G01N 33/543; C12N 5/00
(52) U.S. Cl. ............................ 435/7.1; 435/4; 435/7.72; 435/325; 435/326; 435/327; 435/330; 435/331; 435/7.92; 530/350; 530/351; 530/387.1; 530/387.7; 530/387.9
(58) Field of Search .................................. 530/350, 351, 530/387.1, 387.7, 387.9; 435/7.1, 4, 7.72, 326, 325, 327, 330, 331, 7.92

(56) References Cited

U.S. PATENT DOCUMENTS 5,929,224 * 7/1999 Suzuki et al. .

FOREIGN PATENT DOCUMENTS 723016 7/1996 (EP) .
8140683 6/1996 (JP) .

OTHER PUBLICATIONS

Campbell, Ailsa. Monoclonal antibody technology. Laboratory Techniques in Biochemistry and Molecular Biology 13:1–32, 1984.*

Yamagoe, S. et al. "Identification of a novel chemotactic protein for polymorphonuclear leukocytes produced by a human T cell leukemia cell line", Journal of Interferon Research, (1993) vol. 13, p.S76.

Yamagoe, S. et al. "Purification and primary amino acid sequence of a novel neutrophil chemotactic factor LECT2", Immunology Letters, (Aug., 1996) vol. 52–1, p.9–13.

Yamagoe, S. et al. "Novel homologous polymorphonuclear leukocytes activating proteins (LECT2) derived from human T–cell leulemia SKW–3 cells", 9th International Congress of Immunology, Jul. 23–29, 1995.

* cited by examiner

*Primary Examiner*—Sheela Huff
*Assistant Examiner*—Alana M. Harris
(74) *Attorney, Agent, or Firm*—Davis & Bujold, P.L.L.C.

(57) ABSTRACT

An antibody reacting specifically with human LECT2. This antibody is produced by hybridoma clones G2A5D7 (Accession No. FERM P-15638), A1G1C6 (Accession No. FERM P-15639), 5C5 (Accession No. FERM P-15640), H12D10D6 (Accession No. FERM P-15641), etc. Human LECT2 can be assayed by reacting human LECT2 successively with an immobilized antibody which has been formed by binding the above-mentioned antibody to an insoluble support and a labeled antibody which has been formed by labeling another antibody reacting with human LECT2 with a labeling agent, and then determining the amount of label in the reaction product.

8 Claims, 6 Drawing Sheets

Detection of LECT2 protein by ELISA (A)

(B)

SEQUENCE LISTING

<160> NUMBER OF SEQ ID NOS: 10

<210> SEQ ID NO 1
<211> LENGTH: 151
<212> TYPE: PRT
<213> ORGANISM: Homo sapiens
<220> FEATURE:
<223> OTHER INFORMATION: residue 58 is either Valine or Isoleucine

<400> SEQUENCE: 1

```
Met Phe Ser Thr Lys Ala Leu Leu Ala Gly Leu Ile Ser Thr Ala
 1               5                  10                  15

Leu Ala Gly Pro Trp Ala Asn Ile Cys Ala Gly Lys Ser Ser Asn Glu
                20                  25                  30

Ile Arg Thr Cys Asp Arg His Gly Cys Gly Gln Tyr Ser Ala Gln Arg
            35                  40                  45

Ser Gln Arg Pro His Gln Gly Val Asp Xaa Leu Cys Ser Ala Gly Ser
        50                  55                  60

Thr Val Tyr Ala Pro Phe Thr Gly Met Ile Val Gly Gln Glu Lys Pro
65                  70                  75                  80

Tyr Gln Asn Lys Asn Ala Ile Asn Asn Gly Val Arg Ile Ser Gly Arg
                85                  90                  95

Gly Phe Cys Val Lys Met Phe Tyr Ile Lys Pro Ile Lys Tyr Lys Gly
                100                 105                 110

Pro Ile Lys Lys Gly Glu Lys Leu Gly Thr Leu Leu Pro Leu Gln Lys
            115                 120                 125

Val Tyr Pro Gly Ile Gln Ser His Val His Ile Glu Asn Cys Asp Ser
        130                 135                 140

Ser Asp Pro Thr Ala Tyr Leu
145                 150
```

<210> SEQ ID NO 2
<211> LENGTH: 1092
<212> TYPE: DNA
<213> ORGANISM: Homo sapiens

<400> SEQUENCE: 2

```
aaatcaaata gctatccatg gaatattaga acttgacttg ctccatcctc ttaaactttt      60
tgtgtctcac actaaagaaa tgagagatgc agaattctaa ggctaaatag ctaggaagta     120
ttcattcaaa cttgaatatc ttcaaagaga gtgtggggc aactctaatc agaggaagaa     180
actaaaggaa gtaaaaccag atgttttcca ccaaagccct ccttttggct ggtctgattt     240
ctaccgcact ggcagggcca tgggctaata tatgtgctgg caagtcttcc aatgagatcc     300
ggacgtgtga ccgccatggc tgtggacagt actctgctca agaagtcag aggcctcacc      360 agggtgtgga cgtcttgtgc tctgctggat ctactgtgta cgcaccattc actggaatga     420
ttgtgggcca ggagaaacct tatcaaaaca agaatgctat caataatggt gttcgaatat     480
ctggaagagg tttttgtgtc aaaatgttct acattaagcc aattaagtat aaaggtccta     540
ttaagaaggg agaaaaactt ggaactctat tgcccttgca gaaagtttat cctggcatac     600
aatcgcatgt gcacattgaa aactgtgact cgagtgaccc tactgcatac ctgtaaatcg     660
aaggccaatg gtcagatctt caaaataaaa agtcatctta aaaacctgga tgcatacccct    720 tctcttcaag aaatttgtgt tcacaaaaga aaaatgcatg aagggatgga taccccattt     780
tccatgacat gattattaca cattgcatgc ctgtatcaaa acatctcacg tacctcataa     840
```

-continued

```
acatatacac ctatgtaccc acaaaaattt tttaattaaa aaaggaaat ttgagtttaa        900 atagaaacat gataaatgca agaaagaaaa cattttgatt ttaactcatt gtcactctga       960
tgttcatgtg aactggttgc ttcgggctct ttgatctgtc acctatggaa tctgagtggt      1020 tttattttt agatttctca gtcccaaga tctaagataa ataaacaaga gaacttaaaa        1080
aaaaaaaaaa aa                                                          1092

<210> SEQ ID NO 3
<211> LENGTH: 1092
<212> TYPE: DNA
<213> ORGANISM: Homo sapiens

<400> SEQUENCE: 3
aaatcaaata gctatccatg gaatattaga acttgacttg ctccatcctc ttaaactttt        60
tgtgtctcac actaaagaaa tgagagatgc agaattctaa ggctaaatag ctaggaagta       120
ttcattcaaa cttgaatatc ttcaaagaga gtgtgggggc aactctaatc agaggaagaa       180
actaaaggaa gtaaaaccag atgttttcca ccaaagccct ccttttggct ggtctgattt       240
ctaccgcact ggcagggcca tgggctaata tatgtgctgg caagtcttcc aatgagatcc       300
ggacgtgtga ccgccatggc tgtggacagt actctgctca agaagtcag aggcctcacc       360 agggtgtgga catcttgtgc tctgctggat ctactgtgta cgcaccattc actggaatga       420
ttgtgggcca ggagaaacct tatcaaaaca agaatgctat caataatggt gttcgaatat       480
ctggaagagg ttttgtgtc aaaatgttct acattaagcc aattaagtat aaaggtccta       540
ttaagaaggg agaaaaactt ggaactctat tgcccttgca gaaagtttat cctggcatac       600
aatcgcatgt gcacattgaa actgtgact cgagtgaccc tactgcatac ctgtaaatcg       660
aaggccaatg gtcagatctt caaaataaaa agtcatctta aaaacctgga tgcataccct       720
tctcttcaag aaatttgtgt tcacaaaaga aaatgcatg aagggatgga taccccatt        780 tccatgacat gattattaca cattgcatgc ctgtatcaaa acatctcacg tacctcataa       840
acatatacac ctatgtaccc acaaaaattt tttaattaaa aaaggaaat ttgagtttaa        900 atagaaacat gataaatgca agaaagaaaa cattttgatt ttaactcatt gtcactctga       960
tgttcatgtg aactggttgc ttcgggctct ttgatctgtc acctatggaa tctgagtggt      1020 tttattttt agatttctca gtcccaaga tctaagataa ataaacaaga gaacttaaaa        1080
aaaaaaaaaa aa                                                          1092

<210> SEQ ID NO 4
<211> LENGTH: 41
<212> TYPE: PRT
<213> ORGANISM: Artificial Sequence
<220> FEATURE:
<223> OTHER INFORMATION: Description of Artificial Sequence: primer
      sequence

<400> SEQUENCE: 4

Gly Ala Thr Gly Thr Ser Cys Thr Arg Thr Gly Cys Thr Cys Tyr Gly
  1               5                  10                  15

Ala Thr Gly Gly Ser Thr Cys Tyr Ala Cys Trp Gly Thr Ser Thr Ala
                 20                  25                  30

Thr Gly Cys Tyr Cys Cys Tyr Thr Thr
             35                  40

<210> SEQ ID NO 5
```

-continued

```
<211> LENGTH: 47
<212> TYPE: DNA
<213> ORGANISM: Artificial Sequence
<220> FEATURE:
<223> OTHER INFORMATION: Description of Artificial Sequence:primer
      sequence

<400> SEQUENCE: 5
ggcgaattcg aaaacctgta ttttcagggg ccctgggcta atatatg              47

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:primer
      sequence

<400> SEQUENCE: 6
cgcaagcttt tacaggtatg cagtag                                     26

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:primer
      sequence

<400> SEQUENCE: 7
gcgggatccc cgggccatgg gctaatat                                   28

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:primer
      sequence

<400> SEQUENCE: 8
cgcggatcct tacaggtatg cagtag                                     26

<210> SEQ ID NO 9
<211> LENGTH: 98
<212> TYPE: PRT
<213> ORGANISM: Bovine

<400> SEQUENCE: 9

Gly Pro Trp Ala Ile Ile Cys Ala Gly Lys Ser Ser Asn Glu Ile Arg
 1               5                  10                  15

Thr Cys Asp Gly His Gly Cys Gly Gln Tyr Thr Ala Gln Arg Asn Gln
            20                  25                  30

Lys Leu His Gln Gly Val Asp Val Leu Cys Ser Asp Gly Ser Thr Val
        35                  40                  45

Tyr Ala Pro Phe Thr Gly Ile Met Gly Gln Glu Lys Pro Tyr Lys Asn
    50                  55                  60

Ile Ser Gly Gly Gly Phe Cys Ile Lys Tyr Lys Gly Ser Ile Val Tyr
65                  70                  75                  80

Pro Gly Ile Gln Ser His Ile His Ile Glu Asn Cys Asp Leu Ser Asp
                85                  90                  95

Pro Thr
```

```
<210> SEQ ID NO 10
<211> LENGTH: 14
<212> TYPE: PRT
<213> ORGANISM: Homo sapiens

<400> SEQUENCE: 10

Asp Val Leu Cys Ser Asp Gly Ser Thr Val Tyr Ala Pro Phe
 1               5                  10
```

ANTI-HUMAN LECT2 ANTIBODY, CELLS PRODUCING THE SAME, AND METHOD AND KIT FOR ASSAYING THE SAME

TECHNICAL FIELD

This invention relates to antibodies which react with a new protein, human LECT2, hybridomas for producing the antibodies, and a method and a kit for measuring the human LECT2.

BACKGROUND ART

Recently, neutrophils became known to participate in the damage of cancer cells. As some cancer tissues are observed to have been infiltrated with neutrophils, it is believed that neutrophils respond to chemotactic factors secreted from cancer cells.

LECT2 (Leukocyte-derived chemotaxin 2) was discovered during the search for such chemotactic factors secreted from cancer cells, and this seems to be a chemotactic factor which has been obtained from a culture supernatant of T-cell leukemia cell SKW-3.

Human LECT2 was newly discovered as a protein having equal to or more than 90% homology to bovine LECT2 based on human cDNA libraries, using DNA coding LECT2 in bovine serum which is included in a culture supernatant of T-cell leukemia cell SKW-3. From the following Table 1, the amino acid sequence of the human LECT2 can be compared with that of the bovine LECT2.

TABLE 1

|  | 1 |  |  |  | 5 |  |  |  |  | 10 |  |  |  |  | 15 | SEQ ID NO:1 |
|---|---|---|---|---|---|---|---|---|---|---|---|---|---|---|---|---|
| HUMAN LECT2 | Met | Phe | Ser | Thr | Lys | Ala | Leu | Leu | Leu | Ala | Gly | Leu | Ile | Ser | Thr | |
| BOVINE LECT2 | | | | | | | | | | | | | | | | |
| | | | | | 20 | | | | | 25 | | | | | 30 | SEQ ID NO:9 |
| HUMAN LECT2 | Ala | Leu | Ala | Gly | Pro | Trp | Ala | Asn | Ile | Cys | Ala | Gly | Lys | Ser | Ser | |
| BOVINE LECT2 | Gly | Pro | Trp | Ala | Ile | Ile | Cys | Ala | Gly | Lys | Ser | Ser | | | | SEQ ID No: 9 |
| | | | | | 35 | | | | | 40 | | | | | 45 | |
| HUMAN LECT2 | Asn | Glu | Ile | Arg | Thr | Cys | Asp | Arg | His | Gly | Cys | Gly | Gln | Tyr | Ser | |
| BOVINE LECT2 | Asn | Glu | Ile | Arg | Thr | Cys | Asp | Gly | His | Gly | Cys | Gly | Gln | Tyr | Thr | |
| | | | | | 50 | | | | | 55 | | | | | 60 | |
| HUMAN LECT2 | Ala | Gln | Arg | Ser | Gln | Arg | Pro | His | Gln | Gly | Val | Asp | Val | Leu | Cys | |
| BOVINE LECT2 | Ala | Gln | Arg | Asn | Gln | Lys | Leu | His | Gln | Gly | Val | Asp | Val | Leu | Cys | |
| | | | | | 65 | | | | | 70 | | | | | 75 | |
| HUMAN LECT2 | Ser | Ala | Gly | Ser | Thr | Val | Tyr | Ala | Pro | Phe | Thr | Gly | Met | Ile | Val | |
| BOVINE LECT2 | Ser | Asp | Gly | Ser | Thr | Val | Tyr | Ala | Pro | Phe | Thr | Gly | | Ile | Met | |
| | | | | | 80 | | | | | 85 | | | | | 90 | |
| HUMAN LECT2 | Gly | Gln | Glu | Lys | Pro | Tyr | Gln | Asn | Lys | Asn | Ala | Ile | Asn | Asn | Gly | |
| BOVINE LECT2 | Gly | Gln | Glu | Lys | Pro | Tyr | Lys | Asn | | | | | | | | |
| | | | | | 95 | | | | | 100 | | | | | 105 | |
| HUMAN LECT2 | Val | Arg | Ile | Ser | Gly | Arg | Gly | Phe | Cys | Val | Lys | Met | Phe | Tyr | Ile | |
| BOVINE LECT2 | | | Ile | Ser | Gly | Gly | Gly | Phe | Cys | Ile | Lys | | | | | |
| | | | | | 110 | | | | | 115 | | | | | 120 | |
| HUMAN LECT2 | Lys | Pro | Ile | Lys | Tyr | Lys | Gly | Pro | Ile | Lys | Lys | Gly | Glu | Lys | Leu | |
| BOVINE LECT2 | | | | | Tyr | Lys | Gly | Ser | Ile | | | | | | | |
| | | | | | 125 | | | | | 130 | | | | | 135 | |
| HUMAN LECT2 | Gly | Thr | Leu | Leu | Pro | Leu | Gln | Lys | Val | Tyr | Pro | Gly | Ile | Gln | Ser | |
| BOVINE LECT2 | | | | | | | | | Val | Tyr | Pro | Gly | Ile | Gln | Ser | |
| | | | | | 140 | | | | | 145 | | | | | 150 | (SEQ ID NO:9) |
| HUMAN LECT2 | His | Val | His | Ile | Glu | Asn | Cys | Asp | Ser | Ser | Asp | Pro | Thr | Ala | Tyr | |
| BOVINE LECT2 | His | Ile | His | Ile | Glu | Asn | Cys | Asp | Leu | Ser | Asp | Pro | Thr | | | |
| | 151 | | | | | | | | | | | | | | | |
| HUMAN LECT2 | Leu | | | | | | | | | | | | | | | (SEQ ID NO: 1) |
| BOVINE LECT2 | | | | | | | | | | | | | | | | |

Since the human LECT2 is believed to be a chemotactic factor similar to the bovine LECT2 and its applications to grasping disease conditions and to treatment of cancer are expected, a method for measuring the human LECT2 has been desired to be established.

At first, the bovine LECT2 and the human LECT2 used to be called LECT2a and LECT2b, respectively. However, these names were thought to be inappropriate and therefore changed.

The present invention is presented in respect of the aforementioned background, aiming to provide antibodies against human LECT2, cells for producing them and a method and a kit for measuring the human LECT2.

SUMMARY OF THE INVENTION

In order to solve the aforementioned problem, the antibodies of the first invention specifically react with human LECT2 (a protein having an amino acid sequence indicated in SEQ ID NO: 1 in the sequence table). Such antibodies include, for example, an antibody produced by hybridoma clone G2A5D7 (Accession No. FERM P-15638), an antibody produced by hybridoma clone A1G1C6 (Accession No. FERM P-15639), an antibody produced by hybridoma clone 5C5 (Accession No. FREM P-15640), an antibody produced by hybridoma clone H12D10D6 (Accession No. FERM P-15641) and an antibody produced by hybridoma clone 89F2 (Accession No. FERM P-16229).

The hybridomas of the second invention are characterized by their production of the antibodies which specifically react with the human LECT2. Such hybridomas include, for example, hybridoma clones G2A5D7 (Accession No. FERM P-15638), A1G1C6 (Accession No. FERM P-15639), 5C5 (Accession No. FERM P-15640), H12D10D6 (Accession No. FERM P-15641) and 89F2 (Accession No. FERM P-16229).

A measuring method of the human LECT2 of the third invention characteristically includes the following procedures from a) to c) and from d) to f):
a) The human LECT2 as a standard material is reacted with an immobilized antibody obtained by affixing a first antibody which specifically reacts with the human LECT2 to an insoluble support medium;
b) then, the product is reacted with a labeled antibody obtained by labeling a second antibody which specifically reacts with the human LECT2 with a labeling substance;
c) and a calibration curve is prepared by measuring the quantity of the labeling substance in this reaction product; and
d) said immobilized antibody is reacted with a specimen;
e) then, reacted with said labeled antibody;
f) the quantity of the labeling substance in this reaction product is measured, and the quantity of the human LECT2 contained in the specimen is measured from said calibration curve.

A kit for measuring the human LECT2 of the fourth invention comprises an immobilized antibody which is obtained by affixing an insoluble support medium with a first antibody which specifically reacts with the human LECT2, and a labeled antibody which is obtained when a labeling substance is labeled to a second antibody which specifically reacts with the human LECT2.

In the third and fourth invention, the first antibody is the antibody produced by hybridoma clone G2A5D7 (Accession No. FERM P-15638), the anti body produced by hybridoma clone A1G1C6 (Accession No. FERM P-15639), the antibody produced by hybridoma clone 5C5 (Accession No. FERM P-15640), the antibody produced by hybridoma clone H12D10D6 (Accession No. FERM P-15641) or the antibody produced by hybridoma clone 89F2 (Accession No. FERM P-16229). The second antibody is any one of said four antibodies, but preferably different from the first one. Also, the labeling substance, for example, may be chosen from a group of peroxidase, biotin, β-D-galactosidase, alkaline phosphatase and microperoxidase.

BRIEF DESCRIPTION OF THE DRAWINGS

The file of this patent contains at least one drawing executed in color. Copies of this patent with color drawings will be provided by the Patent and Trademark Office upon request and payment of the necessary fee.

BEST MODE FOR CARRYING OUT THE INVENTION

Figure 1:
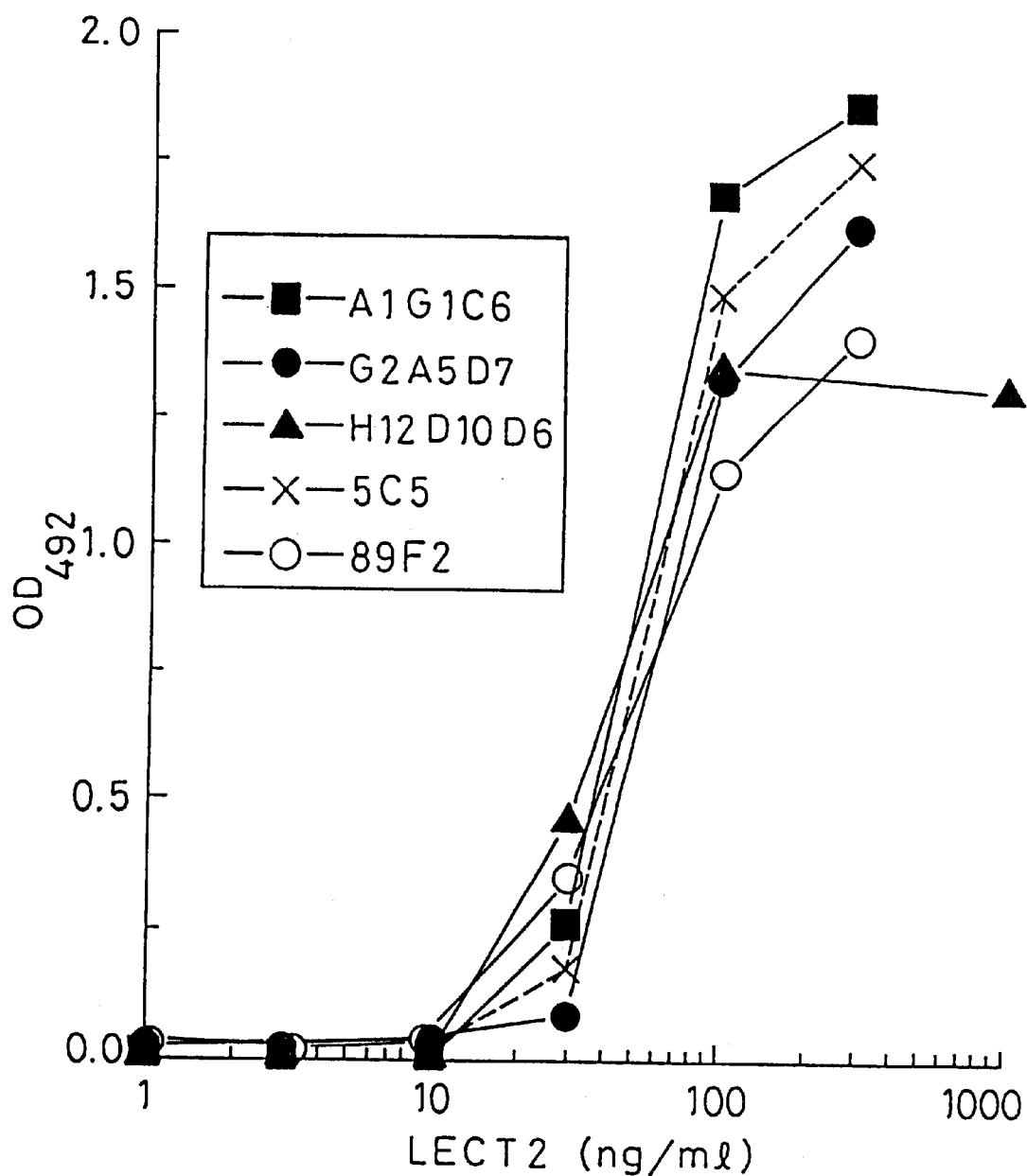
FIG. 1 is a graph showing a detecting result of human LECT2 by ELISA method.

[Antibody which Specifically Reacts with Human LECT2, and Hybridoma which Produces the Antibody]

Procedures for producing an antibody which specifically reacts with the human LECT2 are described as follows.

A. Antigen

The human LECT2 (a protein having an amino acid sequence in the order shown in SEQ ID NO: 1) was cloned and used as an antigen.

B. Immunity by Aforementioned Antigen

As immune animals, mammals such as mice, rats and hamsters can be used. In general, mice are used the most frequently, and BALB/c mice and mice of other strains can be used. In this case, the immune plan and the concentration of an antigen should be chosen so as to produce lymphatic corpuscles which have received enough antigen stimulation. For example, the antigen (25 g for each time) is injected to the abdominal cavity of a mouse for immunization once every two weeks for a total of three injections, and then to the vein. A few days after the final immunization, cells are taken out from the spleen for fusion.

C. Cell Fusion

The spleen is taken out in an axenic way from the individual mammal which has thus been immunized. A unicellular suspension is prepared from it. Cell fusion between the spleen cells (antibody producing cells) and appropriate myeloma cells is carried out using an appropriate cell fusion accelerator. The myeloma cells of a mammal which belongs to the same species as the immunized animal are preferred, however, spleen cells of a rat, a hamster or the like can also be fused with the myeloma cells of a mouse. The preferred ratio of spleen cells to myeloma cells is in the range between about 20:1 and about, 2:1. It is appropriate to use 0.5–1.5 ml fusion medium for spleen cells of about $10^8$.

As a preferred fusion accelerator, for example, polyethylene glycol of mean molecular weight from 1000 to 4000 can be advantageously used. Other fusion accelerators known in this field (Sendai virus (so-called HVJ), for example) can also be used. The cell fusion may also be carried out by using an electric shock method, apart from the method using such fusion accelerators.

D. Selection of Hybridomas which Produce Specific Antibodies

A mixture of unfused spleen cells, unfused myeloma cells and fused syncytia (referred to herein as hybridomas) is diluted in a separate vessel (a microtiterplate, for example) with a selection medium which does not support the unfused myeloma cells, and cultured for a time sufficient to kill the unfused cells (for about 1 hour). A drug resistant culture medium (8-azaguanine resistant, for example) which does not support the unfused myeloma cells (HAT culture medium, for example) is used. In this culture medium, the unfused myeloma cells die. The unfused spleen cells are non-neoplastic and therefore die after some definite time (1 week later). To the contrary, the fused cells can survive in the selection medium because they have both neoplastic properties of the parent cells of myeloma and properties of parent spleen cells.

Then, after hybridomas are detected, antibodies against the aforementioned human LECT2 are screened by Enzyme Linked Immunosorbent Assay, and only hybridomas producing monoclonal antibodies which specifically react with the human LECT2 are selected. Such hybridomas include, for example, hybridoma clone G2A5D7 (Accession No. FERM P-15638), hybridoma clone A1G1C6 (Accession No. FERM P-15639), hybridoma clone 5C5 (Accession No. FERM P-15640), hybridoma clone H12D10D6 (Accession No. FERM P-15641) and hybridoma clone 89F2 (Accession No. FERM P-16229).

F. Production of Specific Antibodies

After cloning in an appropriate method (limiting dilution analysis, for example) the hybridomas which produce the specific antibodies, the antibodies can be produced by two different methods. According to the first method, hybridomas are cultured in an appropriate culture medium for a predetermined time, and then the monoclonal antibodies produced by the hybridomas can be obtained from the culture supernatant. According to the second method, hybridoma cells can be injected to the abdominal cavity of an immune animal having isogenic or semi-isogenic genes. The monoclonal antibodies produced by the hybridomas can be obtained from blood and abdominal dropsy of the host animal.

[Method of Measuring Human LECT2 in a Sample]

A. Preparation of Immobilized Antibodies

In order to obtain immobilized antibodies produced by affixing antibodies which specifically react with the human LECT2 to insoluble support mediums, the antibodies and the insoluble support mediums are brought into contact, by which the antibodies are adsorbed on the surfaces of the insoluble support mediums. A chemical procedure such as the covalent bonding is also useful for combining them. As the insoluble support mediums, for example, high polymers such as polystyrene, polyethylene, polypropylene, polyester, polyacrylonitrile, fluorine polymer, cross-linked dextran and polysaccharide can be shown, as well as paper, glass, metal, agarose and combinations of these materials. As the form of the insoluble support mediums, various forms can be adapted like a tray, sphere, rod, fiber, plate, vessel, cell, test tube and so on.

B. Preparation of Labeled Antibodies

An antibody which specifically reacts with the human LECT2 may be either IgG or a fragment of Fab, $F(ab)'_2$ or the like.

The labeling substance is not limited if it can be used for ordinary immunological measuring methods, however, enzymes, avidins, fluorescent substances, luminescent substances, radioactive substances and the like are preferably used. As enzymes, peroxidase, $\beta$-D-galactosidase, alkaline phosphatase, microperoxidase can be used, as fluorescent substances, fluorescent isothiocyanate, phicobiliprotein, phicoerythrine and the like can be used, as luminescent substances, isolucinol, lucigenine and the like can be used and as radioactive substances, $^{125}I$, $^{131}I$, $^{14}C$, $^{3}H$ and the like can be used. When biotin is used as a labeling substance further with avidin labeled with an enzyme, a high sensitivity can be preferably obtained. In this case, an enzyme similar to that labeled to the antibody can be used as a labeling enzyme, peroxidase being especially preferable.

When an enzyme is used as a labeling substance, a substrate and, if needed, a coloring substance is used, in order to measure the activity thereof. When peroxidase is used as an enzyme, $H_2O_2$ is used as a substrate, and ammonium salt of 2,2'-azino-di-[3-ethylbenzylthiazoline sulphonic acid](ABTS), 5-aminosalicylic acid, o-phenylenediamine (OPD), 4-aminoantipyrine, 3,3',5,5'-tetramethylbenzidine or the like can be used as a coloring substance. When alkaline phosphatase is used as an enzyme, o-nitrophenylphosphate or the like is used as a substrate. When $\beta$-D-galactosidase is used as an enzyme, fluorescent di-($\beta$-D-galactopyranose), 4-methylunberypheryl-$\beta$-D-galactopyranose or the like can be used as a substrate.

C. Generation of Calibration Curve

Standards consisting of predetermined amounts of human LECT2 are reacted with the antibody, and then the human LECT2 which has specifically reacted with the immobilized antibody is reacted with the labeled antibody. Subsequently, the quantity of the labeling substance of the labeled antibody is measured. By this procedure, the relation between the amount of the human LECT2 in the standards and the labeling substance detected is represented in a calibration curve. The calibration curve is then used to determine the amount of LECT2 in a specimen, as described below.

Reagents used in this immunodiagnostic method are preferably solutions which range from pH 6.0 to 8.0, including, for example, buffer solutions of phosphoric acid, of tris-hydrochloric acid and of acetic acid and the like. Solutions which are suitable for use in this method are provided in the Exemplification section below.

D. Measurement of Human LECT2 in a Specimen

Human LECT2 in a specimen is then determined using the same reagents as used to generate the calibration curve. The specimen is reacted with the immobilized antibody, and then reacted with the labeled antibody. In this stage, the amount of labeled antibody which binds depends on the concentration of the human LECT2 of the specimen. Subsequently, the quantity of the labeling substance in the labeled antibody is measured. The measured value is used to correlate the concentration of human LECT2 present in the specimen using the calibration curve. And as the result, the concentration of the human LECT2 in the specimen is determined.

[Kit for Measuring Human LECT2]

The kit for measuring the human LECT2 comprises:
(1) an immobilized antibody which reacts with the human LECT2, produced as described above; and
(2) a labeled second antibody which specifically reacts with the human LECT2, produced as describe above. The kit may optionally include other reaction medium and/or standards containing predetermined amounts of human LECT2. Moreover, when the labeling substance of the labeled antibody is an enzyme, a reaction-terminating solution and a substrate for measuring the activity of the enzyme are usually included. The aforementioned measuring method can be carried out using this measuring kit.

Preferred embodiments of the invention will now be described with reference to the drawings. However, the embodiment of this invention is not restricted to the following embodiments, and can be variously modified within the scope of the invention.

Exemplification

[Embodiment 1] Preparation of Immunogen (Human LECT2)

[1-1] Cloning of Human LECT2 and Determination of Nucleotide Sequence of Cloned Human LECT2

The cloning of the human LECT2 cDNA was carried out as follows.

Poly $A^+$ RNA was prepared by treating the T cell-type leukemia cell SKW-3 with PHA-P (50 µg/ml) (made by DIFCO Inc.). The first strand cDNA (1st cDNA) was synthesized using poly $A^+$ RNA (5 µg) and oligo-dT as a primer.

Then, a primer of PCR was synthesized based on the partial amino acid sequence of bovine LECT2 (its amino acid sequence is shown in SEQ ID NO: 9). Namely, 6 kinds of oligonucleotides were deduced from the amino acid sequence WAIICA (amino acids 3–8 of SEQ ID NO: 9) to form 5' primer, and 4 kinds of oligonucleotides were deduced from the amino acid sequence HIENCD (amino acids 88–93 of SEQ ID NO: 9) to form 3' primer. The DNA fragment was amplified by the 24 reactions which are the combinations of said primers using the 1st cDNA as a template according to PCR method. The amplified DNA was separated with agarose gel using DNA probe (GATGTC/GCTA/GTGCTCT/CGATGGC/GTCT/CACT/AGTC/GTATGCT/CCCT/CTT: Refer to SEQ ID NO: 4), based on amino acid sequence DVLCSDGSTVYAPF (SEQ ID NO: 10), and analyzed by Southern blotting method. As the result, about 370 bp of DNA fragments were detected, which were cloned into pUC19.

As the result of screening a cDNA library made from human liver using the cloned cDNA fragment as a probe, twelve positive clones were obtained among 1.3 million clones. All these clones proved to be classified into two types by the analysis of restriction enzymes, and the base sequence of the clone of the longest cDNA fragment of each group was determined. The sequence analysis of the longest clones of each type suggested that the two types of cDNA would be derived from an identical gene which had two poly A signals on the 3' end. The amino acid sequence of the coded protein revealed that the amino acid sequences were 90% homologous to the determined bovine LECT2 amino acid sequence. Then, this protein, considered to be encoded by the open reading frame, was named human LECT2. The amino acid sequence and the base sequence of the human LECT2 are shown in SEQ ID NO: 1 and 2, respectively.

[1-2] Constitution of Recombinant Plasmid Containing Human LECT2 Gene

Based on the cloned human LECT2 cDNA, GGCGAAT-TCGAAAACCTGTATTTTCAGGGGC-CCTGGGCTAATATATG (Refer to SEQ ID NO: 5) was used as the 5'-primer and CGCAAGCTTTTACAGGTATG-CAGTAG (Refer to SEQ ID NO: 6) was used as the 3'-primer. The DNA fragments including the human LECT2 cDNA were amplified with these primers by PCR using 25 cycles of denaturation at 94° C. for 1 min., annealing at 55° C. for 2 min. and elongation at 72° for 3 min. After digestion with EcoRI and HindIII, the fragments including the human LECT2 cDNA were ligated into the EcoRI/HindIII site of pMAL™-C (Biolab Inc.). Thus recombined plasmid was named pMAL-TEV-human LECT2. This expression vector produces a fusion protein, consisting of the maltose-binding-protein and the human LECT2, in the presence of IPTG, under the control of the lac promoter. A TEV protease (originated from the Tabacco Etch Virus) recognition sequence is located at the coupling site, which enables specific cleavage at that position.

Also, based on the cloned human LECT2 cDNA, GCGG-GATCCCCGGGCCATGGGCTAATAT (Refer to SEQ ID NO: 7) was used as the 5'-primer and CGCGGATCCTTA-CAGGTATGCAGTAG (Refer to SEQ ID NO: 8) was used as the 3'-primer. The DNA fragments including the human LECT2 cDNA were amplified with these primers by PCR using 25 cycles of denaturation at 94° C. for 1 min., annealing at 55° C. for 2 min. and elongation at 72° C. for 3 min. After digesting with BamHI, the fragments containing the human LECT2 cDNA were ligated into the BamHI site of pGEX-3X (Pharmacia Inc.). Thus recombined plasmid was named pGEX-Xa-human LECT2. This expression vector produces a fusion protein of a glutathione-S-transferase and the human LECT2 in the presence of IPTG, under the control of the lac promoter. A Xa protease recognition sequence exists in its coupling site, which enables a specific cleavage at that position.

[1-3] Transformation of *E. Coli* by Recombinant Plasmid Containing Human LECT2 Gene

*E. coli* JM109 was transformed with the recombinant plasmid pMAL-TEV-human LECT2 obtained above. Out of thus obtained *E. coli* clones, those having an expected base sequence were screened by the deoxy method and *E. coli* clone Mal-human LECT2 (Accession No. FERM P-14669: It was transferred to the international deposit under Accession No. FERM BP-5302), containing the expected DNA fragment, was obtained.

[1-4] Production of Human LECT2 by Animal Cells

The 5' side of the human LECT2 cDNA ligated into the BamHI site of pUC19 from HindIII to EcoRI was deleted by exonuclease III until −14 base sequence, treated with T4 DNA polymerase to form a smooth end group, ligated with Pstl linkers, fragmented with Pstl and Bgl II and ligated into the Pstl/BamHI site of the expression vector pcDL-SRα294. This recombinant expression vector was transfected into CHO cells of a Chinese hamster, and one strain which highly expresses the human LECT2 (C1D8-1) (Accession No. FERM P-14668: It was transferred to the international deposit under Accession No. FERM BP-5301) was obtained.

(Determination of Molecular Size)

The recombinant human LECT2 (expression of animal cells) was detected by metabolically labeling it with $^{35}$S-methionine and subjecting the culture supernatant of CHO cells to SDS gel electrophoresis, giving two bands of molecular size of about 14 kDa and 16 kDa. (The 16 kDa band is main. The two bands seem to have appeared because of differences in processing.)

[Embodiment 2] Immunity

The immunogen, human LECT2, prepared in the aforementioned Embodiment 1, (100 µl) was mixed sufficiently with Freund's complete adjuvant (100 µl) to give a suspension, which was injected to the abdominal cavities of two mice (male BALB/c), 25 µl to each as the immunogen. Further, the immunogen of the same quantity was injected 5 times, every other week. Then, three days later the spleens were taken out and subjected to a fusion experiment.

Separately, two rabbits were also immunized in the same manner. After serum was separated from the blood taken out from the rabbits, absorption operation was carried out using an ordinary method, and the IgG fraction was separated to produce a polyclonal antibody.

[Embodiment3] Cell Fusion and Selection and Acquisition of Hybridomas which Produce Specific Monoclonal Antibodies The spleen cells taken out from the mice (10 parts) and myeloma cells (SP-2/O-Ag-14) from mice of the same strain (1 part) were mixed, and cell fusion was carried out using 50% polyethylene glycol 4000 as a fusion accelerator. The fused cells were suspended in the HAT culture medium (culture medium containing hypoxanthine, aminopterin and thymidine) containing 10% bovine serum so as to give the cell concentration of $1 \times 10^6$ cells/ml, and poured to 96 wells of microtiterplate (Maxisoap made by Nunk Inc.: Same ones were used hereafter), by 100 µl for each well.

The hybridomas were cultured in $CO_2$ incubator (5% $CO_2$, 37° C.), transferred to the HAT culture medium, conditioned in the HAT culture medium, and further conditioned in the 10% FCS-RPMI 1640 culture medium.

The antibodies in the supernatant of the fused and cultured cells were detected, using a microtiterplate on which the human LECT2 protein was immobilized, by ELISA method. Cloning was carried out two times for every well which proved to be positive, using the limiting dilution analysis. Then, 5 kinds of clones which had reactivity to the human LECT2 were selected, and named G2A5D7, A1G1C6, 5C5, H12D10D6 and 89F2, respectively (Accession Nos. FERM P-15638, FERM P-15639, FERM P-15640, FERM P-15641 and FERM P-16229, respectively).

Each clone obtained was suspended in the 90% bovine serum including 10% DMSO and kept in liquid nitrogen. The monoclonal antibody produced by each clone was amplified in the abdominal cavity of a mouse. Each antibody from the abdominal dropsy was purified with a protein-A cephalose column.

[Embodiment 4] Confirmation of Specificity of Monoclonal Antibodies

1. Confirmation of Specificity by ELISA Method

A PBS solution of the human LECT2 (1–1000 ng/ml) was prepared. The human LECT2 was immobilized on a microtiterplate using the solution, reacted with the antibody solution of each clone, and then reacted with the anti-mouse immunoglobulin labeled with peroxidase (made by Cappel Inc.). Optical absorbance at the wave length of 492 nm was measured for each product in a solution of orthophenylene diamine and hydrogen peroxide as a substrate. The results are shown in FIG. 1.

It was confirmed that each clone specifically reacts with the human LECT2 from the fact that the value of optical absorbance increased with the concentration of the immobilized human LECT2 and became constant above some concentration.

2. Confirmation of Specificity by Western Blotting

A mixture of the human LECT2 and the maltose-binding-protein (MBP), as an antigen, was subjected to SDS-polyacrylamide gel electrophoresis (PAGE) (16.5% mono-acrylamide/bis-acrylamide; 3% bis-/mono-acrylamide+bis). After the electrophoresis, a specificity of the reaction was confirmed by Western blotting. The monoclonal antibody of each clone showed reactivity at about 16 kD, and did not react with the MBP. The results are shown in FIG. 2.

Figure 2:
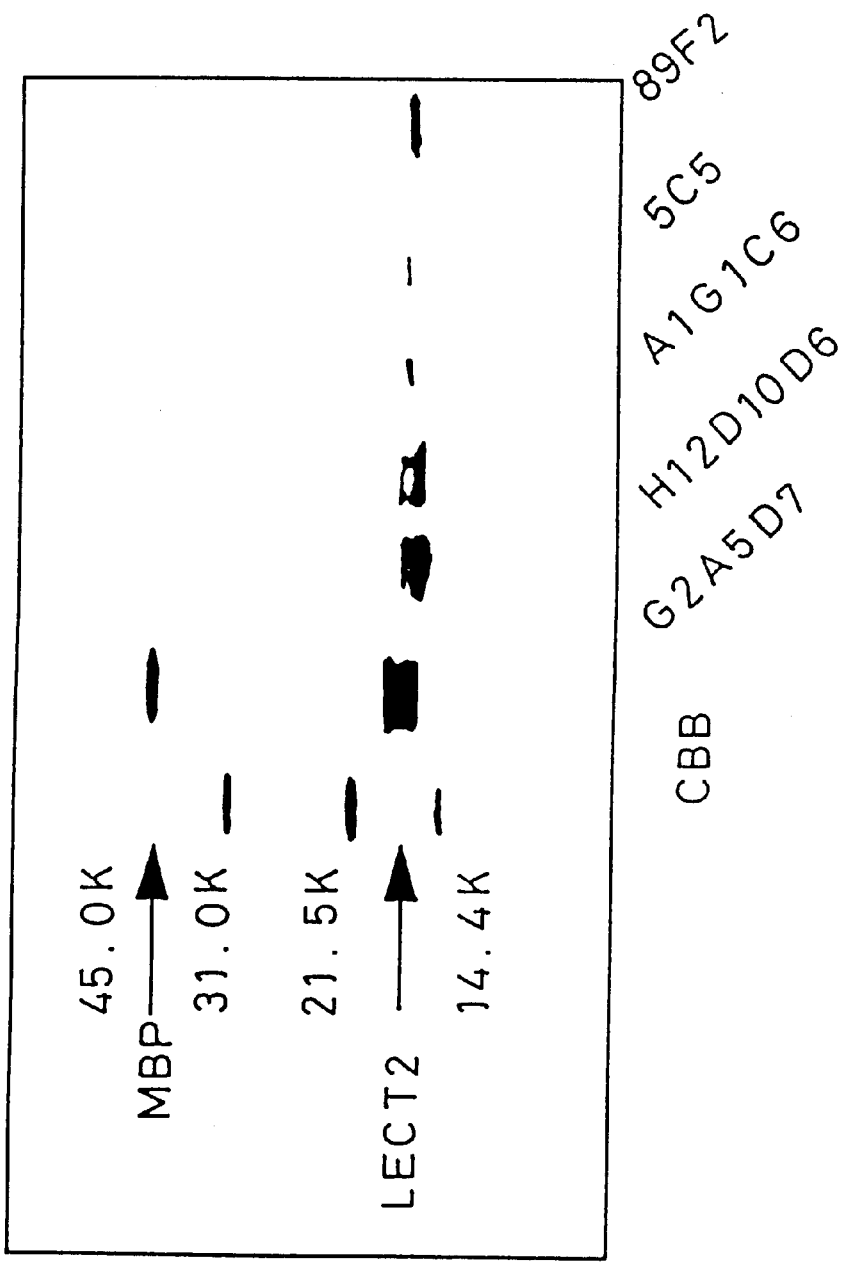
FIG. 2 is an exemplary view showing the reaction specificity of the monoclonal antibody of each clone by Western blotting.

In FIG. 2, CBB is the abbreviation of coomassie brilliant blue and shows protein dyeing. The first lane is a molecular size marker and the others are electrophoresis results of the human LECT2+MBP, as an antigen. The first and second lanes show the protein dyeing and the others show Western blot for each monoclonal antibody.

[Embodiment 5] Confirmation of Subclass by ELISA Method

For each monoclonal antibody obtained in the aforementioned Embodiment 3, the class- subclass was confirmed using a monoclonal subclass isotyping kit made by American Corlex Inc. The result was that clones A1G1C6 and G2A5 were IgG2b and clone H12D10 was IgM. However, clones 5C5 and 89F2 were not confirmed.

[Embodiment 6] Immobilization of Antibodies

The solution of monoclonal antibody clone G2A5, obtained in the aforementioned Embodiment 3, was prepared at the concentration of 5 µl/ml, using 0.1M carbonate buffer (pH 9.0), poured on 96 wells of microtiterplate by 100 µl for each well, and reacted stationarily at 4° C. for 20 hours. The antibody solution was eliminated from the wells, 200 µl of PBS containing 1% BSA and 5% sucrose was added to each well and blocking was carried out at room temperature (20–25° C.) for 2 hours in the stationary state. The blocking liquid was discarded and the plate was air-dried to produce immobilized antibodies. The immobilized antibodies were kept sealed with desiccant.

[Embodiment 7] Preparation of Labeled Antibodies

Purified IgG of the polyclonal antibody, obtained in the aforementioned Embodiment 2, was added with ficin at 0.056 U per 1 mg purified IgG, reacted at 37° C. for 8 hours, and subjected to gel filtration using Ultrogel ACA44, and Fab' fraction was thus obtained. This Fab' fraction was labeled with peroxidase by the maleimide method to give peroxidase-labeled antibodies. Specifically, the labeling was carried out following "Measuring Method of Enzyme Immunity, the Third Edition," published by Igakushoin and written by Eiji Ishikawa.

[Embodiment 8] Measurement of Human LECT2

Figure 3:
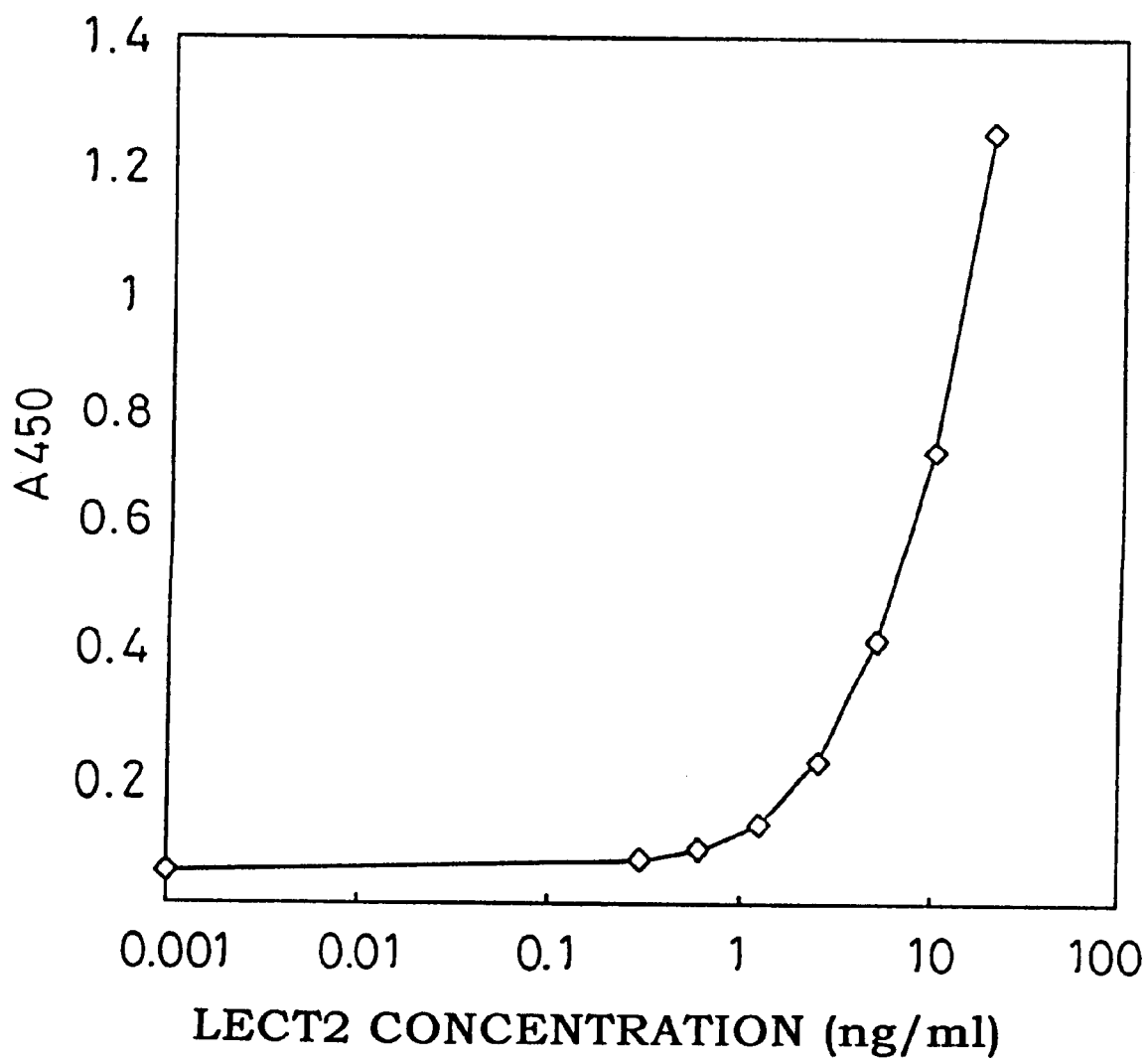
FIG. 3 is a graph showing the relation between the concentration of human LECT2 and optical absorbance.

The human LECT2 protein was diluted with PBS to give 0.001–20 ng/ml solutions. 200 µl of each solution was added to each well of the plate with the immobilized antibodies obtained in the aforementioned Embodiment 6, and reacted at room temperature for 1 hour. After each well was washed with 300 µl of PBS 4 times, excessive PBS was removed. Then, each well was provided with the peroxidase-labeled antibodies (100 µl) obtained in the aforementioned Embodiment 7, reacted at room temperature for 1 hour, washed again with PBS, added and reacted with a solution of tetramethyl benzidine and hydrogen peroxide (100 µl), and the reaction was terminated by adding 100 µl of 1.5N phosphoric acid. Then, the optical absorbance at the wave length of 450 nm was measured. The results of measurement are shown in Table 2 and FIG. 3.

TABLE 2

| Std. conc. (ng/ml) | A450 |
|---|---|
| 0.001 | 0.05 |
| 0.3 | 0.07 |
| 0.6 | 0.085 |
| 1.25 | 0.125 |
| 2.5 | 0.22 |
| 5 | 0.41 |
| 10 | 0.73 |
| 20 | 1.25 |

From the results, the relation of the quantity of the labeled substance to that of the human LECT2 is obtained, that is, a calibration curve is prepared. By using the calibration curve, the relation of the quantity of the labeled substance to that of the human LECT2 in a specimen is obtained, that is, a calibration curve is prepared, which is used to determine the quantity of the human LECT2 contained in the specimen.

Figure 4:
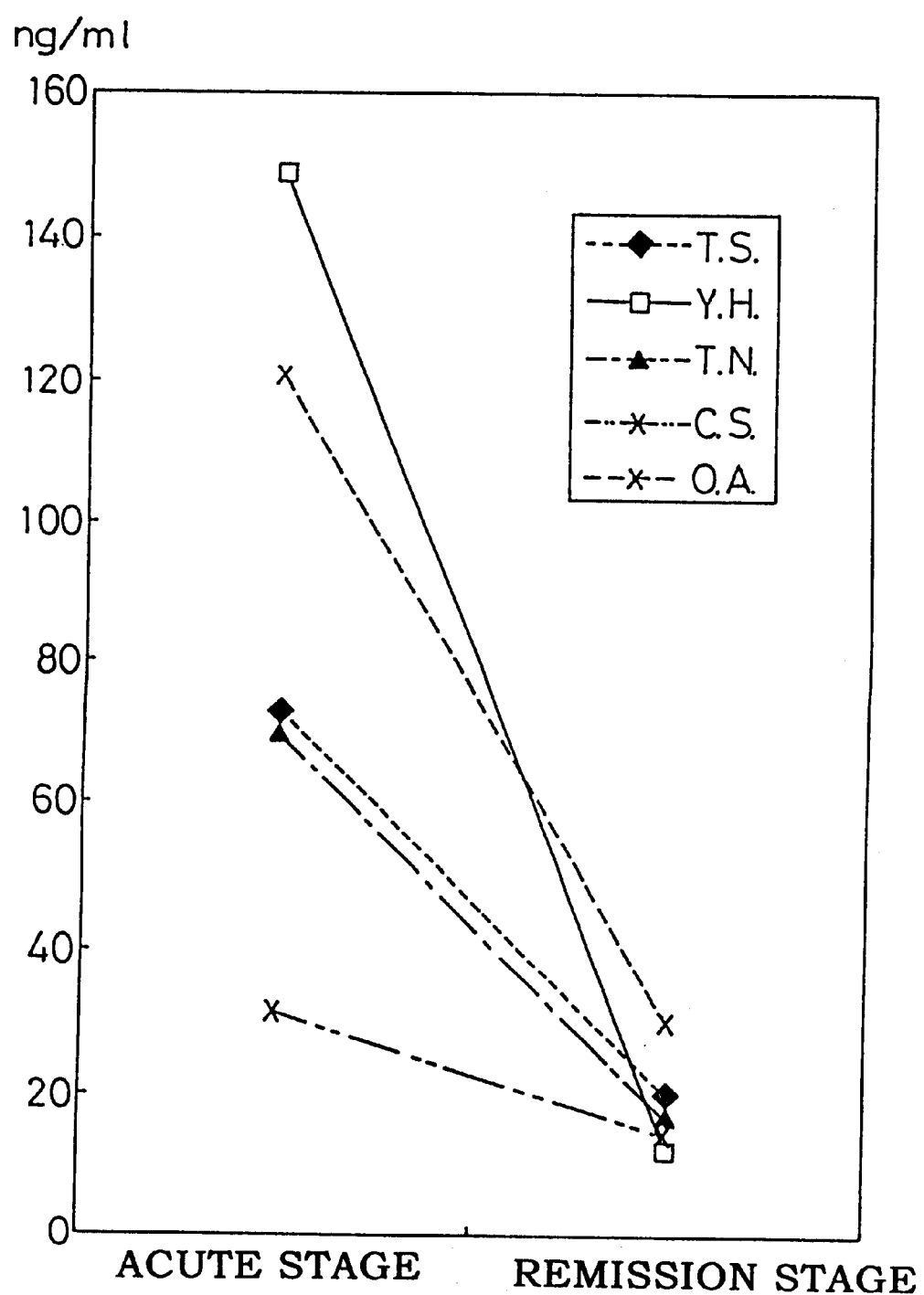
FIG. 4 is a graph showing measured human LECT2 values of specimens obtained from patients with acute hepatitis in an acute stage and in a remission stage.

For specimens from patients with acute hepatitis, data of a comparison of measured values at acute stages and at remission stages are shown in Table 3 and FIG. 4.

TABLE 3

| Specimen | Disease | Disease Condition | Measured value (ng/ml) |
|---|---|---|---|
| T.S. | HA (B-type) | Acute Stage | 73 |
|  |  | Remission Stage | 21 |
| Y.H. | HA (B-type) | Acute Stage | 149 |
|  |  | Remission Stage | 13 |
| T.N. | HA (B-type) | Acute Stage | 70 |
|  |  | Remission Stage | 18 |
| C.S. | HA (C-type) | Acute Stage | 32 |
|  |  | Remission Stage | 15 |
| O.A. | HA (resistant) | Acute Stage | 121 |
|  |  | Remission Stage | 31 |

As the result of a preliminary study on the measured series, it was proven that the human LECT2 in specimens lost its antigenicity at a comparatively early stage, especially, in serum the antigenicity disappeared promptly. Therefore, plasma was used as a specimen. Plasma was obtained by quickly separating the blood after blood collection and stored in a frozen state at −20° C. or lower until measurement. When a specimen is not diluted by more than 5 times, there is a possibility that measured values are influenced. Therefore, all specimens were measured after 10 fold dilution.

Comparison of the measured values of each specimen at its acute stage and at its remission stage shows distinct decline of human LECT2 amounts in the remission stage compared to that of the acute stage. From this result, the concentration of the human LECT2 in specimens is thought to reflect the disease conditions of patients.

As the content of the human LECT2, a chemotactic factor, in a specimen can be measured in this way, the result of measurement can be used to diagnose disease conditions and to treat the disease.

[Embodiment 9] Immunostaining Tissue

Liver tissue samples obtained from a person in good health and also from a hepatitis patient, were subjected to formalin fixation using a routine method, and embedded in paraffin. The paraffin-embedded tissues were cut with a microtome into tissue sections. Deparafinization of the tissue sections was carried out by a routine method. About 100 $\mu$l of PBS solution of IgG fraction (5 $\mu$g/ml), obtained by purifying monoclonal antibody clone 89F2 in Embodiment 3, was poured on the tissue sections, reacted at 37° C. for 30 minutes and the tissue sections were washed with PBS. The sections were then reacted with the anti-mouse IgG labeled with peroxidase (made by Daco Inc.) at 37° C. for 30 minutes, washed again with PBS and, subsequently, dyed by reacting with a solution of 3,3',5,5'-diamino benzidine and hydrogen peroxide. The nuclei were dyed with hematoxylin.

Figure 5A:
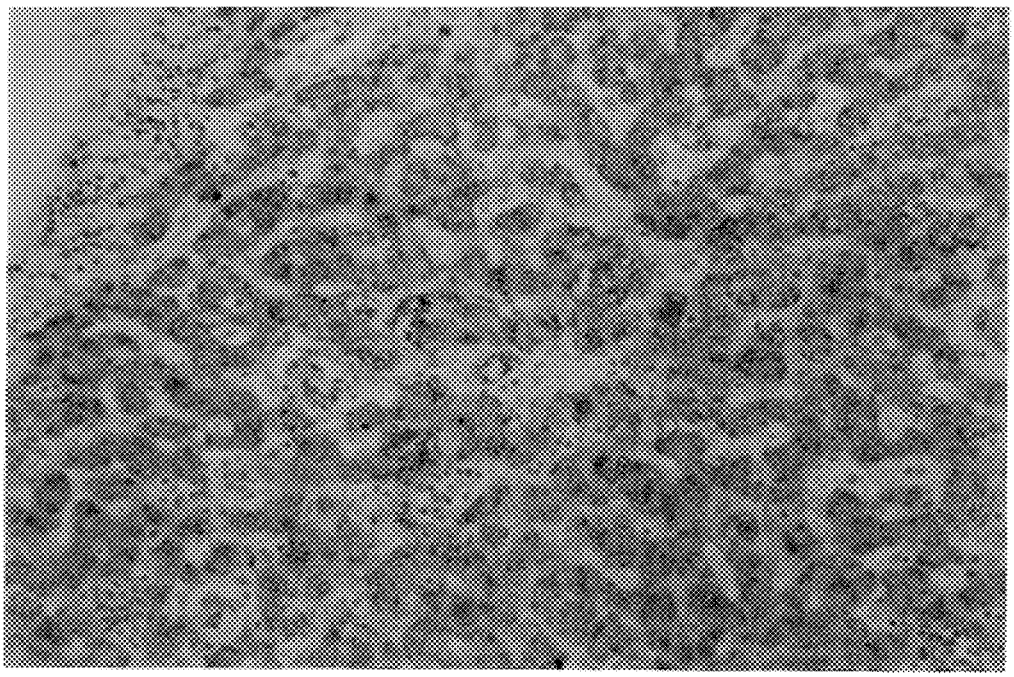
FIG. 5 consists of photographs of dyed tissues of a person in good health, wherein (A) is magnified by 100 times and (B) is magnified by 200 times.
Figure 5B:
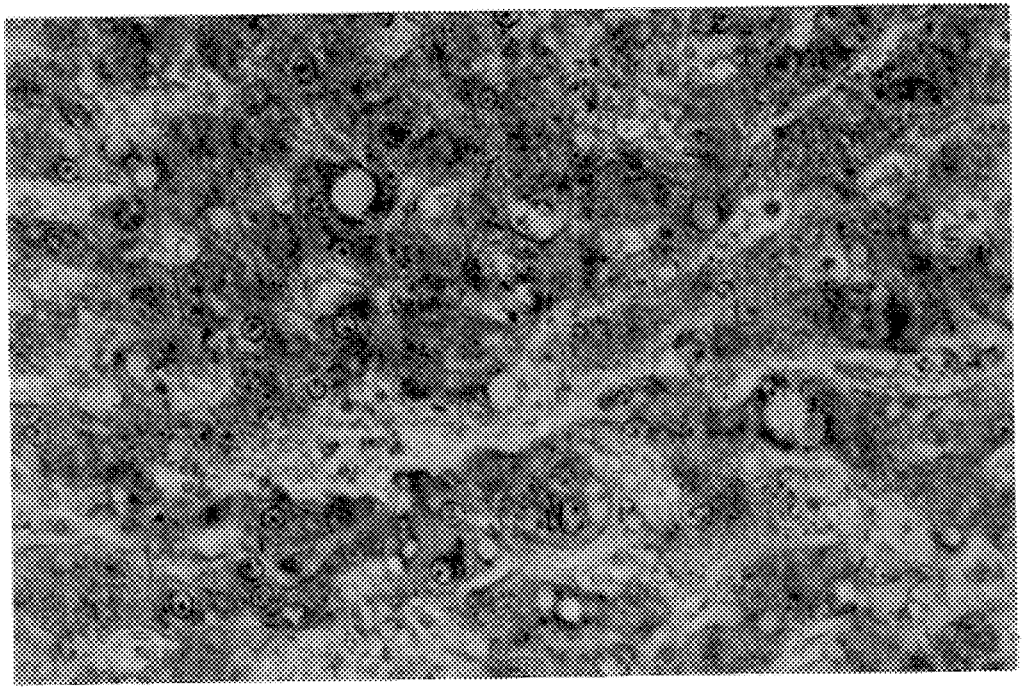
Figure 6:
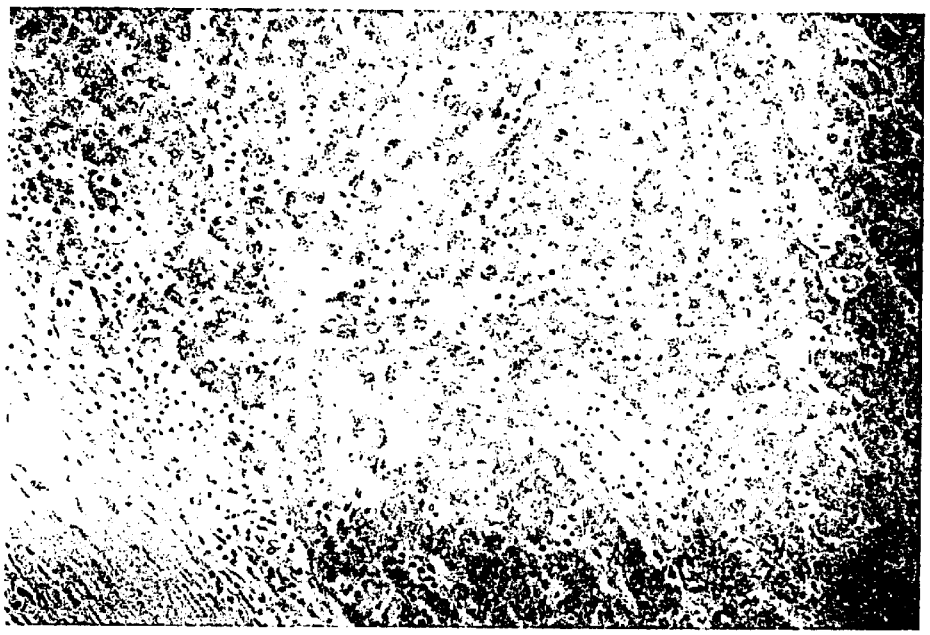
FIG. 6 consists of photographs of dyed tissues of a patient with cirrhosis, wherein (A) is magnified by 100 times and (B) is magnified by 200 times.
Figure 6:
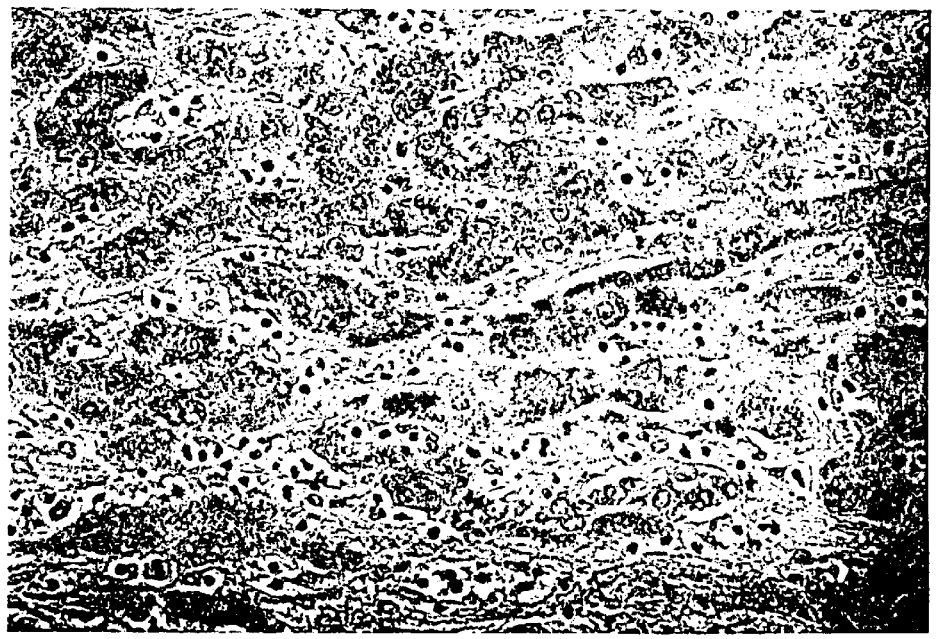

FIG. 5 contains photographs showing the dyed images of the tissue samples of a person in good health; (A) is a photograph magnified by 100 times and (B) is a photograph magnified by 200 times. FIG. 6 contains photographs showing the dyed images of the tissue samples from a hepatitis patient; (A) is a photograph magnified by 100 times and (B) is a photograph magnified by 200 times.

Diffuse staining was observed on the cytoplasm of liver cells from both a person in good health and a hepatitis patient. Specifically, for both the person in good health and the hepatitis patient, granular staining (shown as brown) by diaminobenzidine was observed on liver parenchyma cells, but for the hepatitis patient, mixtures of positive and negative cells were confirmed and the staining pattern was different from that of the person in good health (for the person ill good health, liver parenchyma cells were all positive). Staining of connective tissues was not observed. The particles which appear as blue spots in FIGS. 5 and 6 are nuclei. This result suggests that the LECT2 has some relation with the cell cycle.

Possibility of Indusrtial Use

The antibody against the human LECT2 of this invention is useful to the immunological medical treatment and diagnosis, and useful in the industrial fields related thereto. The hybridoma of this invention is also useful for obtaining the antibody against the human LECT2. Furthermore, the antibody against the human LECT2 of this invention can be used for a method and a kit for measuring the human LECT2. As the human LECT2 (thought to be a chemotactic factor) contained in a specimen can be measured using the method and the kit for measurement, it becomes effectively possible to use and apply the result of measurement to aid in disease diagnosis and treatment. In more detail, for example, the antibody of this invention is reacted with the tissues taken out from the patients of various diseases, (hepatitis and cirrhosis, for example) and the sites in the tissues where the cells manifesting the human LECT2 are located can be examined. Accordingly, the method and the kit of the invention can be extended to the diagnosis and treatment of various diseases.

Depositary Institution

C1D8-1 and Mal-human LECT2 were deposited with the following international depositary institution, under the following accession numbers and deposit dates, respectively.

Name of institution: National Institute of Bioscience and Human-Technology, Agency of Industrial Science and Technology, Ministry of International Trade and Industry Address: 1-3, Higashi 1-chome, Tsukuba city, Ibaraki pref., Japan (Zip Cord 305)

Accession Number and Deposit Date:
(1) C1D8-1
  FERM BP-5301: Nov. 25, 1994
(2) Mal-human LECT2
  FERM BP-5302: Nov. 25, 1994

Hybridoma clones, G2A5D7, A1G1C6, 5C5, H12D10D6 and 89F2 were deposited with the following domestic depositary institution, under the following accession numbers and deposit dates, respectively.

Name of institution: National Institute of Bioscience and Human-Technology, Agency of Industrial Science and Technology, Ministry of International Trade and Industry Address: 1-3, Higashi 1-chome, Tsukuba city, Ibaraki pref., Japan (Zip Cord 305)

Accession Number and Deposit Date:
(1) Hybridoma clone G2A5D7
  FERM BP-6489: May 21, 1996
(2) Hybridoma clone A1G1C6
  FERM P-15639: May 21, 1996
(3) Hybridoma clone 5C5
  FERM P-15640: May 21, 1996
(4) Hybridoma clone H12D10D6
  FERM P-15641: May 21, 1996
(5) Hybridoma clone 89F2
  FERM P-16229: May 19, 1997

What is claimed is:

1. An antibody which specifically binds human LECT2 having the amino acid sequence listed in SEQ ID NO: 1, wherein the antibody is produced by hybridoma clone G2A5D7 (Accession No. FERM BP-6489).

2. A hybridoma clone G2A5D7 (Accession No. FERM BP-6489).

3. A method for quantitatively detecting human LECT2 having the amino acid sequence listed in SEQ ID NO: 1 in a specimen obtained from an individual, the method comprising:

a) providing:
      i) an insoluble support to which is bound an antibody which specifically binds the human LECT2;
      ii) a labeled antibody which specifically binds the human LECT2;
   b) contacting the insoluble support with a solution made from a specimen containing the human LECT2 under conditions appropriate for antibody binding;
   c) washing the insoluble support of step b) under conditions which preserve antibody binding;
   d) contacting the washed insoluble support of step c) with the labeled antibody under conditions appropriate for antibody binding;
   e) washing the insoluble support of step d) under conditions which preserve antibody binding;
   f) quantitatively detecting the label on the labeled antibody which is bound to the washed insoluble support of step e);
   g) correlating the amount of label determined in step f) to a specific amount of human LECT2 using a standard calibration curve to determine the amount of human LECT2 in the specimen.

4. The method of claim 3, wherein the antibody bound to the insoluble support and the labeled antibody are not the same antibody.

5. A kit for quantitatively detecting human LECT2 having the amino acid sequence listed in SEQ ID NO: 1 in a solution, comprising:

a) an insoluble support to which is bound an antibody which specifically binds the human LECT2; and
   b) a labeled antibody which specifically binds the human LECT2.

6. The kit of claim 5, wherein the antibody bound to the insoluble support and the labeled antibody are not the same anitbody.

7. The method of claim 3, wherein the individual has been diagnoseded with, or undergoing therapy for, liver disease.

8. The kit of claim 5 wherein the solution contains a specimen obtained from a patient diagnosed with, or undergoing therapy for, liver disease.

* * * * *